United States Patent
Schröder

(10) Patent No.: US 10,633,314 B2
(45) Date of Patent: Apr. 28, 2020

(54) METHOD FOR THE CONVERSION OF ABIENOL TO SCLAREDIOL

(71) Applicant: GIVAUDAN SA, Vernier (CH)

(72) Inventor: Fridtjof Schröder, Hettlingen (CH)

(73) Assignee: GIVAUDAN S.A., Vernier (CH)

( * ) Notice: Subject to any disclaimer, the term of this patent is extended or adjusted under 35 U.S.C. 154(b) by 0 days.

(21) Appl. No.: 15/554,157

(22) PCT Filed: Mar. 17, 2016

(86) PCT No.: PCT/EP2016/055854
§ 371 (c)(1),
(2) Date: Aug. 28, 2017

(87) PCT Pub. No.: WO2016/146769
PCT Pub. Date: Sep. 22, 2016

(65) Prior Publication Data
US 2018/0072644 A1   Mar. 15, 2018

(30) Foreign Application Priority Data
Mar. 19, 2015 (GB) .................... 1504646.9

(51) Int. Cl.
| | |
|---|---|
| C07D 307/92 | (2006.01) |
| C07C 29/48 | (2006.01) |
| C07C 35/36 | (2006.01) |
| C07C 67/293 | (2006.01) |

(52) U.S. Cl.
CPC .............. *C07C 29/48* (2013.01); *C07C 35/36* (2013.01); *C07C 67/293* (2013.01); *C07D 307/92* (2013.01); *C07C 2601/02* (2017.05); *C07C 2602/28* (2017.05); *Y02P 20/55* (2015.11)

(58) Field of Classification Search
CPC ....... C07C 29/48; C07C 35/36; C07C 67/293; C07C 2601/02; C07C 2602/28; C07D 307/92; Y02P 20/55
USPC ......................................................... 549/458
See application file for complete search history.

(56) References Cited

FOREIGN PATENT DOCUMENTS

| EP | 0170955 A2 | 2/1986 |
|---|---|---|
| ES | 2044780 A1 | 1/1994 |

OTHER PUBLICATIONS

Wikipedia, Plug flow reactor model, Dec. 2013, p. 1-4. (Year: 2013).*
International Search Report and Written Opinion of the International Searching Authority for corresponding application PCT/EP2016/055854 dated Jun. 14, 2016.
GB Search Report for corresponding application GB 1504646.9 dated Jan. 12, 2016.
A. F. Barrero, et al., "Synthesis of Abrox (R) from (−)-sclareol and (+)-cis-abienol", Tetrahedron, Elsevier Science Publishers, Amsterdam, NL, vol. 49, No. 45, Jan. 1, 1993, pp. 10405-10412.
A. F. Barrero, et al., "Degradation of the Side Chain of (−)-Sclareol: A Very Short Synthesis of nor-Ambreinolide and Ambrox", Synthetic Communications, Taylor & Francis Inc., Philadelphia, PA; US, vol. 34, No. 19, Jan. 1, 2004, pp. 3631-3643.
J. A. Giles, et. al., "Turkish Tobacco-1 Isolation and Characterization of a- and B-Levantenolide", Tetrahedron, vol. 14, pp. 246-251, 1961.

* cited by examiner

*Primary Examiner* — Taylor V Oh
(74) *Attorney, Agent, or Firm* — Norris McLaughlin, P.A.

(57) ABSTRACT

A method of selective conversion of Abienol, represented by formula 1, to Sclareodiol, represented by formula 2

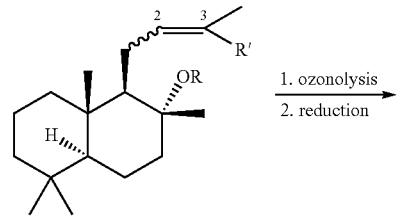

1
1a: R = H, R' = ——CH═CH$_2$
1b: R = H, R' = ——CH$_2$—CH$_3$
1c: R = Ac, R' = ——CH═CH$_2$
1d: R = H, R' = ——cyclopropyl

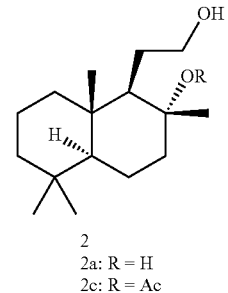

2
2a: R = H
2c: R = Ac by ozonolysis and subsequent reduction. The ozonolysis is carried out at temperatures above −60° C., preferably in nonhalogenated solvents. R is selected from H, acetals, aminals, optionally substituted alkyl groups, such as benzyl group, carboxylates such as acetates or formates, carbonates such as methyl or ethyl carbonates, carbamates, and any protecting group which can be attached to 1 and cleaved from 2, R' is selected from CH═CH$_2$, an alkyl moiety with C2-C20, e.g. CH$_2$—CH$_3$, or a cycloalkyl or polycycloalkyl moiety with C3-C20, e.g. cyclopropyl, optionally alkylated, respectively, and the wavy bond is depicting an unspecified configuration of the adjacent double bond between C2 and C3.

15 Claims, No Drawings

METHOD FOR THE CONVERSION OF ABIENOL TO SCLAREDIOL

The present application is filed under 35 USC 371 based on PCT/EP2016/055854 filed 17 Mar. 2016, which in turn claims the priority benefit of GB 1504646.9 filed 19 Mar. 2015. The present application claims all available priority benefit to the foregoing, and incorporates the entirety of their disclosures herein.

This invention relates generally to methods of preparing perfumery raw materials and to key intermediates used in, or prepared during such methods. In particular, this invention relates to a novel method for the preparation of (−)-Sclareodiol 2a (R=H) or a Sclareodiol derivative 2 from Z-(+)-Abienol 1a (R=H, R'=—CH=CH$_2$) or an Abienol derivative 1. (−)-Sclareodiol 2a is an important intermediate that can be further cyclized to the compound of formula 3, also known as (−)-Ambrox® ((3aR,5aS,9aS,9bR)-3a,6,6,9a-tetramethyldodecahydro-naphtho[2,1-b]furan), an important base note in perfumery, particularly useful as a substitute for Ambergris. The compound of formula 3 is also commercially available under further trade names as Ambroxan®, Ambrofix® or Amberoxide®.

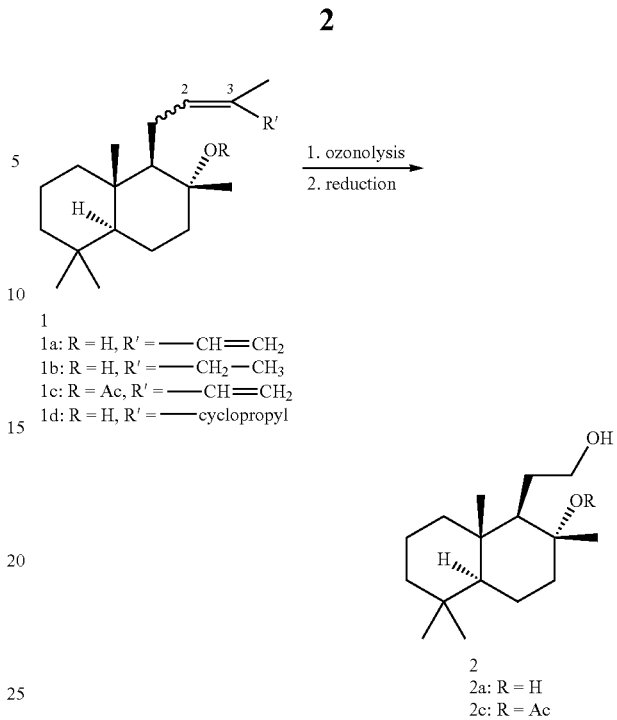

1
1a: R = H, R' = ——CH=CH$_2$
1b: R = H, R' = ——CH$_2$—CH$_3$
1c: R = Ac, R' = ——CH=CH$_2$
1d: R = H, R' = ——cyclopropyl 2
2a: R = H
2c: R = Ac

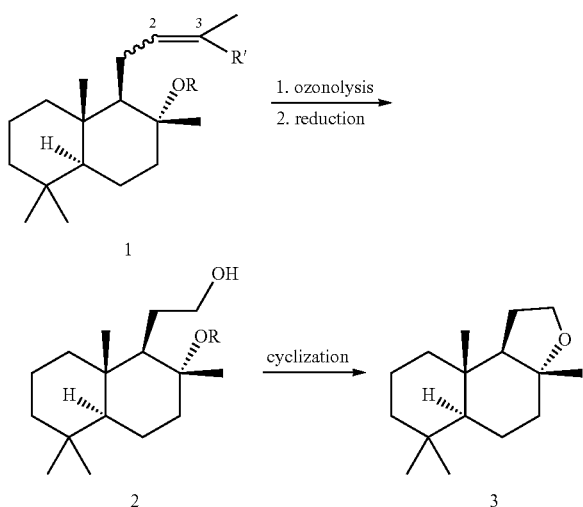

A. F. Barrero et al. (*Tetrahedron* 49, 10405, 1993 and ES 2044780, 1994) describe the ozonolysis of Z-(+)-Abienol 1a at −78° C. in dichloromethane (DCM), followed by reduction of the formed ozonide with lithium aluminumhydride (LAH) in tetrahydrofurane (THF). This might be an efficient procedure to obtain (−)-Sclareodiol 2a on a gram-scale in the laboratory, however, temperatures below −20° C. are difficult to realize and maintain on industrial scale. Furthermore, an excess of LAH is necessary to reduce the ozonide and its byproducts. Additionally, the solvents DCM and THF add further complexity, because DCM is removed from the inherently explosive ozonide before THF is added, whereas emissions and waste water release of especially DCM is problematic.

Applicant surprisingly has found that it is possible to convert selectively a compound of formula 1 to a compound of formula 2 by ozonolysis and subsequent reduction, wherein the ozonolysis is carried out at temperatures above −60° C. In the presented formulae 1 and 2, R is selected from H, acetals, aminals, optionally substituted alkyl groups, such as benzyl group, carboxylates such as acetates or formates, carbonates such as methyl or ethyl carbonates, carbamates, or any protecting group that can be readily attached before and cleaved after ozonolysis and reduction. In formula 1, R' is selected from CH=CH$_2$, an alkyl moiety with C2-C20, e.g. CH$_2$—CH$_3$, or a cycloalkyl or polycycloalkyl moiety with C3-C20, e.g. cyclopropyl, optionally alkylated, respectively. The wavy bond is depicting the unspecified configuration of the adjacent double bond between C2 and C3, which is usually in the Z-configuration, but may also be in the E-configuration, or the compound of formula 1 is used as E/Z-mixture.

The subsequent reduction step is preferably carried out on the crude product obtained by the ozonolysis. It is preferred to carry out the subsequent reduction step shortly after the ozonolysis, in particular within 2 hours, even more preferred after 5 to 30 min after the ozonolysis is completed. In a preferred embodiment, the reduction step is performed within seconds up to minutes after completion of the ozonolysis step.

Such a selective conversion of Z-(+)-Abienol 1a or Abienol derivatives 1 to (−)-Sclareodiol 2a or OH-protected Sclareodiol 2, respectively, can thereby be performed under industrially feasible conditions using reaction temperatures above −60° C., giving 2 in 80% yield, preferably in 90% yield, or in 95% yield or higher. These findings were surprising, because at higher temperatures such as −20° C. to +20° C., byproducts were expected which could have decreased yield and purity of 2. In fact, (+)-Sclareolide 4 and Sclaracetal 5 (with R''=alkyl) were detected as byproducts, however, short reaction times and immediate reduction after complete conversion of Abienol 1 to its corresponding ozonide reduced the amount of these byproducts considerably.

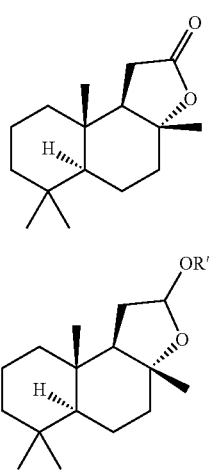

For the subsequent formation of (−)-Ambrox 3, (−)-Sclareodiol 2a is of higher value than (+)-Sclareolide 4, because no further reduction step is required. (+)-Sclareolide 4 is nevertheless another valuable intermediate for the production of (−)-Ambrox 3, as described for example in *Chemie in unserer Zeit* 45, 374 (2011). Byproduct 4 can be therefore converted to (−)-Ambrox 3, e.g. by reduction of (+)-Sclareolide 4 to (−)-Sclareodiol 2a, followed by cyclization to (−)-Ambrox 3 by techniques generally known to the person skilled in the art.

According to the invention, the ozonolysis temperature for the conversion of Z-(+)-Abienol 1a or Abienol derivatives 1 to (−)-Sclareodiol 2a or OH-protected Sclareodiol 2 can be above −60° C., preferably above −40° C., and ideally in the range of −20° C. to +20° C., preferentially at 0° C. to +20° C.

The subsequent reduction step is preferably carried out at temperatures above −60° C., preferably above −40° C., and ideally in the range of −20° C. to +20° C., preferentially at 0° C. to +20° C. During the reduction step, the temperature might be different than during the ozonolysis step.

The method of the invention can be carried out in any suitable apparatus. Preferably, the ozonolysis and/or reduction are carried out in a flow reactor, where the residence time of the ozonide is low, and an effective cooling of the very exothermic reaction can be ensured, as explained in S. Hübner, K. Jähnisch et. al. *OPRD* 13, 952 (2009) for example. In a flow reactor it is possible to keep the time between the completion of the ozonolysis step and the reduction step in a range of seconds up to minutes.

The method according to the invention can be carried out in any solvent. Preferably, a suitable solvent can be selected from all non-halogenated solvents or mixtures thereof. The non-halogenated solvents include alcoholic solvents of the type $R^1OH$ including diols and triols, aromatic solvents, esters and ethers, optionally cyclized and/or substituted. Non-halogenated solvents are more ecological in comparison to the halogenated ones, and their disposal is easier to handle.

Preferentially, an alcoholic solvent of the type $R^1OH$, including diols and triols, with $R^1$=H, alkyl, branched alkyl, optionally cyclized and/or substituted are selected. Ethanol is a particularly preferred alcoholic solvent. Mixtures of all these solvents are possible, and co-solvents such as water and/or aromatic solvents, esters and ethers as set forth above can be added at any stage.

Preferably, the same solvent or solvent mixture is employed for ozonolysis and subsequent reduction, without a solvent switch. It is particularly preferred to perform the ozonolysis and reduction in one non-halogenated solvent or a non-halogenated solvent mixture without a solvent switch.

The subsequent reduction may be performed by any suitable reducing agent including aluminum hydrides, borohydrides, boranes, or by heterogenic or homogeneous catalytic hydrogenation. It is preferred to use safe borohydride reducing agents of the type $MBH_4$, e.g. M=Na, K. Inexpensive $NaBH_4$ is particularly preferred.

It is particularly preferred to use $NaBH_4$ as reducing agent in 0.5-5 mol equiv, more preferentially in 2-4 mol equiv, more preferentially in 3 mol equiv or less.

Abienol or Abienol derivatives 1 may be selected as suitable substrates. Z-(+)-Abienol 1a may be obtained from balsam fir (*Abies balsamea*) or tobacco (*Nicotiana tabacum*) by extraction and/or distillation including thin-film and/or steam distillation. Extraction methods have been described for example in *J. Chem. Soc.* 5822 (1964). Z-(+)-Abienol 1a may be also obtained using cis-abienol synthase made by fermentation through metabolic engineering of plants or microorganisms (J. Bohlmann et al. *J. Biol. Chem.* 287, 12121, 2012). These methods provide Z-(+)-Abienol 1a with purities of 10-100%, preferentially 50-100%, usually 50-60%. Z-(+)-Abienol 1a qualities are converted directly to (−)-Sclareodiol 2a (with R=H) by the method of the invention. Any byproducts are separated after ozonolysis and reduction by separation methods known to the chemist skilled in the art.

Suitable Abienol derivatives may also be employed as substrates. Derivatives of Abienol 1 with R≠H may be used in forms in which the OH-function is protected as acetal, aminal, or with alkyl groups, optionally substituted, such as the benzyl group, carboxylates, such as acetates or formates, all of which are optionally substituted, carbonates, such as methyl- or ethylcarbonate, carbamates, or any other substituent, which can be readily cleaved after ozonolysis and reduction. The conversion of such an Abienol derivative 1 to a corresponding derivative of Sclareodiol 2 proceeds with lower amounts of byproducts, such as (+)-Sclareolide 4 in comparison to unprotected Z-(+)-Abienol 1a. After conversion, the protecting group can be removed to yield (−)-Sclareodiol 2a, for example by hydrolysis in the presence of base, that can be further converted to (−)-Ambrox 3.

In a particular embodiment, OH-protected Sclareodiol derivatives can be converted directly to (−)-Ambrox 3, without the deprotection step being necessary. For example, Abienol acetate 1c, obtainable from Z-(+)-Abienol 1a, can be converted to the corresponding sclareodiol acetate 2c, followed by a direct cyclization to (−)-Ambrox 3, using experimental conditions as described for example in WO 2009010791.

Alternatively, the terminal monosubstituted alkene group of Z-(+)-Abienol 1a can be hydrogenated or alkylated prior to ozonolysis giving Abienol derivatives with $R'$=$CH_2$—$CH_3$, or a cyclopropyl moiety, optionally alkylated, respectively. This has the advantage that less ozone, for example 75%, or even only 50% ozone is required for the reduction of the remaining trisubstituted double bond in the 2,3-position of the side chain when compared to Z-(+)-Abienol 1a. Furthermore, less reducing agent, for example 75%, in particular 50% reducing agent is needed for the reduction of the corresponding ozonide. Such Abienol derivatives, for example 1b and 1d, are prepared by methods known to the chemist skilled in the art, e.g. by selective hydrogenation or cyclopropanation of the terminal double bond of Z-(+)-

Abienol 1a. They give (−)-Sclareodiol 2a upon the described conversion of 1 to 2 according to the invention.

Ozonolysis of Z-(+)-Abienol 1a or corresponding derivatives 1 at temperatures above −60° C., ideally in the range of −20° C. to +20° C., preferentially at 0° C. to +20° C. and in non-halogenated solvents followed immediately by reduction of the ozonide gives mainly (−)-Sclareodiol 2a or corresponding derivatives 2 (for example 2c is obtained from 1c) plus minor byproducts such as (+)-Sclareolide 4, Sclaracetal 5 or sclaral acetate 6.

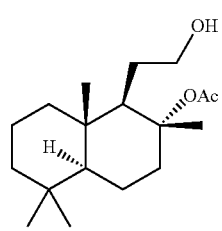

2c

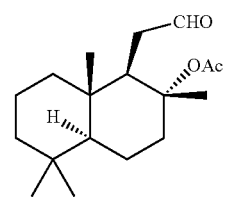

6

Z-(+)-Abienol 1a and Abienol derivatives 1 with a protected OH-function and a modified terminal alkene group are particularly preferred substrates.

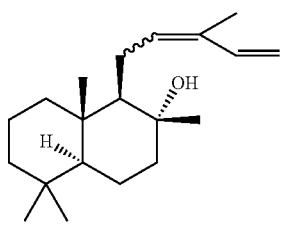

1a

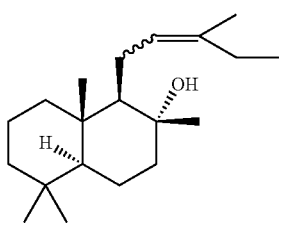

1b

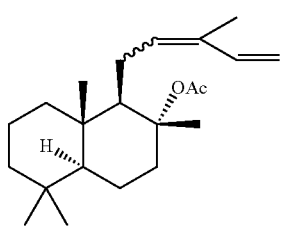

1c

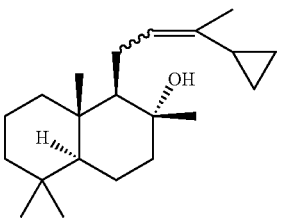

1d

There now follows a series of examples that further act to illustrate the invention.

EXAMPLE 1

Ozonolysis of Z-(1R,2R,4aS,8aS)-2,5,5,8a-tetramethyl-1-(3-methyl-penta-2,4-dien-1-yl)decahydronaphthalen-2-ol 1a at −15° C. Followed by Immediate Reduction of the Ozonide to (1R,2R,4aS,8aS)-1-(2-hydroxyethyl)-2,5,5,8a-tetramethyl-deca-hydronaphthalen-2-ol 2a Ozone (4% in oxygen, 0.25 m$^3$/h) is introduced at −20° C. to −15° C. and under stirring to a yellow cloudy solution of Z-(+)-Abienol 55% 1a (10 g, 19 mmol) in ethanol (100 ml) under strong external cooling. After 30 min (and complete conversion of 1a according to TLC) the ozone feed is stopped, and the reaction flask purged with oxygen for 10 min. The colorless cloudy solution of ozonide in ethanol is added to a suspension of sodium borohydride (2.13 g, 56 mmol) in ethanol (20 ml) between −20° C. and 5° C. under strong external cooling and stirring. After complete addition (and a negative peroxide test) the bright yellow reaction mixture is allowed to warm-up to room temperature and the solvent is partially removed by evaporation. The residue is mixed with ice and water (75 ml) under strong stirring. The resulting milky suspension is extracted with tert-butyl methylether (2×50 ml). The combined organic layers are washed with water (2×50 ml) and conc. NaCl (2×25 ml), dried over MgSO$_4$, filtered and evaporated giving 7.6 g of a light yellow solid which is chromatographed over silicagel (300 g) using a hexane/ethylacetate 66/33 to 100% ethyl acetate gradient giving 0.5 g of (+)-Sclareolide 4 (11%) and 4.15 g (88%) of (−)-Sclareodiol 2a as colorless solids.

The analytical data of (+)-Sclareolide 4 were identical to the ones described for the commercially available compound. The analytical data of (−)-Sclareodiol 2a were identical to the ones described for this compound, e.g. by L. E. Overman et al. *J. Am. Chem. Soc.* 135, 15342 (2013).

EXAMPLE 2 (COMPARATIVE)

Ozonolysis of Z-(+)-Abienol 1a Followed by Conversion of the Ozonide to (+)-Sclareolide 4 and Sclareacetal 5 at Ambient Temperatures Ozone (4% in oxygen, 0.25 m$^3$/h) is introduced at −20° C. to −15° C. and under stirring to a yellow cloudy solution of Z-(+)-Abienol 55% (10 g, 19 mmol) and internal standard dodecane (0.5 g, 2.9 mmol) in ethanol (100 ml) under strong external cooling. After 30 min (and complete conversion of Z-(+)-Abienol 1a according to TLC) the ozone feed is stopped and the reaction flask purged with oxygen for 10 min. The reaction mixture is allowed to warm-up to room temperature. GC-analysis after 67 h at room temperature shows (+)-Sclareolide 4 (25% according to internal standard [istd]). The colorless cloudy solution of ozonide in ethanol is added to a suspension of sodium borohydride (2.13 g, 56 mmol) in ethanol (20 ml) between −20° C. and 5° C. under strong external cooling and stirring. GC-analysis shows (+)-Sclareolide 4 (17% according to istd) and (−)-Sclareodiol 2a (34% according to istd). After a negative peroxide test the bright yellow reaction mixture is mixed with ice and water (75 ml) under strong stirring. The resulting milky suspension is extracted with tert-butyl methylether (2×50 ml). The combined organic layers were washed with water (50 ml) und conc. NaCl (25 ml), dried over MgSO$_4$, filtered and evaporated giving 8.1 g of a yellow oil. The crude product is flash-chromatographed over silicagel (300 g) using a hexane/ethylacetate 66:33 to 100% ethylacetate gradient giving 1.9 g of O-ethyl sclaracetal 5 (19%), 1.25 g (13%) of (+)-Sclareolide 4 and 0.5 g (5%) of (−)-Sclareodiol 2a as colorless solids.

The NMR-data of Sclaracetal 5 (R″=Et, 2 isomers, ratio 72:28) were identical to the ones described by K. Awano et al. in *F&F Journal* 20, 18-21 (2005). MS of 5 (EI): 280 (3%, [M]$^+$), 266 (17%), 265 (66%), 201 (10%), 195 (19%), 191 (30%), 178 (11%), 177 (76%), 175 (10%), 150 (18%), 138 (10%), 137 (54%), 136 (24%), 135 (18%), 125 (51%), 123 (68%), 121 (40%), 119 (14%), 99 (11%), 97 (23%), 96 (23%), 95 (92%), 94 (13%), 93 (36%), 91 (26%), 85 (30%), 83 (23%), 82 (60%), 81 (77%), 80 (11%), 79 (16%), 77 (16%), 71 (20%), 69 (95%), 68 (40%), 67 (57%), 57 (22%), 55 (63%), 53 (18%), 43 (100%), 41 (82%), 29 (78%), 27 (21%). IR (film): 2923 (m), 2867 (m), 1457 (m), 1377 (m), 1330 (w), 1224 (w), 1180 (w), 1115 (m), 1096 (m), 1041 (m), 987 (w), 969 (s), 942 (m), 912 (m), 896 (w), 865 (w), 843 (w).

EXAMPLE 3

Ozonolysis of Z-(+)-Abienol 1a at −60° C. Followed by Quench of the Ozonide Upon NaBH$_4$ Ozone (4% in oxygen, 0.25 m$^3$/h) is introduced at −70° C. to −60° C. and under stirring to a yellow cloudy solution of Z-(+)-Abienol 55% (10 g, 19 mmol) and istd dodecane (0.5 g, 2.9 mmol) in ethanol (100 ml) under strong external cooling. After 30 min (and complete conversion of Z-(+)-Abienol 1a according to TLC) the ozone feed is stopped and the reaction flask purged with oxygen for 10 min. The colorless cloudy solution of ozonide in ethanol is added portionwise to a suspension of sodium borohydride (2.13 g, 56 mmol) in ethanol (20 ml) between −20° C. and 5° C. under strong external cooling and stirring. After a negative peroxide test the bright yellow reaction mixture is mixed with ice and water (75 ml) under strong stirring. The resulting milky suspension is extracted with tert-butyl methyl ether (2×50 ml). The combined organic layers were washed with water (50 ml) und conc. NaCl (25 ml), dried over MgSO$_4$, filtered and evaporated giving 7.75 g of a light yellow semi-solid. The crude product is flash-chromatographed over silicagel (300 g) using a hexane/ethylacetate 66:33 to 100% ethylacetate gradient giving 4 g of (−)-Sclareodiol 2a (84%) and 0.2 g (4%) of (+)-Sclareolide 4 as colorless solids.

EXAMPLE 4

Ozonolysis and Reduction of Z-4,5-Dihydroabienol 1b

Z-(1R,2R,4aS,8aS)-2,5,5,8a-tetramethyl-1-(3-methylpenta-2,4-dien-1-yl)decahydronaphthalen-2-ol) 1b

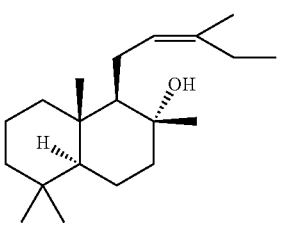

1b

30% H$_2$O$_2$ in water (186 g, 1.64 mol) is added dropwise to a stirred mixture of Z-(+)-Abienol 55% (1a, 50 g, 95 mmol) and hydrazine hydrate (116 g, 2.43 mol) in ethanol (500 ml) at 5-10° C. within 3.5 h. After another hour at this temperature the mixture is poured onto water and ice (500 ml). Extraction with tert-butyl methyl ether (2×250 ml), washing of the combined organic layers with H$_2$O (100 ml), conc. FeSO$_4$ (3×50 ml) and brine (50 ml), drying of the organic phase over MgSO$_4$, filtration and evaporation of the solvents give 44 g of a brown oil which is purified by flash chromatography over silicagel (600 g) using a hexane/tert-butyl methyl ether gradient of 20:1 to 2:1 to give 28.3 g (81-94% corr) of 4,5-dihydroabienol 1b with 77-90% purity.

Analytical data of 1b: $^1$H-NMR (CDCl$_3$, 400 MHz): 5.2 (t, 1H), 2.2 (m, 1H), 2.0-2.2 (3H), 1.85 (1H), 1.7 (s, 3H), 1.5-1.7 (2H), 1.2-1.5 (7H), 1.2 (s, 3H), 1.1-1.2 (m, 1H), 1.0 (t, 3H), 0.9-1.0 (2H), 0.9 (s, 3H), 0.82 (s, 3H), 0.8 (s, 3H) ppm. $^{13}$C-NMR (CDCl$_3$, 400 MHz): 136.4 (s, alkene), 126.8 (d, alkene), 74.4 (s), 61.8 (d), 56.1 (d), 43.7 (t), 42.0 (t), 40.0 (t), 38.8 (s), 33.5 (q), 33.3 (s), 24.9 (t), 24.7 (q), 23.6 (t), 23.2 (q), 21.6 (q), 20.6 (t), 18.6 (t), 15.7 (q), 12.8 (q) ppm. MS (EI): 274 (4%, [M-18]$^+$), 259 (3%, [M-18-15]$^+$), 217 (2%), 191 (10%), 178 (8%), 177 (8%), 163 (7%), 150 (8%), 149 (10%), 137 (20%), 136 (100%), 135 (11%), 123 (13%), 121 (29%), 109 (24%), 108 (11%), 107 (78%), 95 (23%), 93 (14%), 91 (10%), 83 (15%), 82 (10%), 81 (17%), 79 (11%), 69 (18%), 68 (13%), 67 (11%), 55 (28%), 43 (17%), 41 (18%). IR (film): 3441 (br), 2961 (w), 2923 (s), 2868 (m), 1458 (m), 1386 (m), 1339 (m), 1190 (w), 1156 (w), 1124 (m), 1083 (m), 1067 (w), 1031 (w), 1012 (w), 995 (w), 970 (w), 936 (s), 909 (w), 824 (w). The IR data were congruent to the ones described by P. F. Vlad et al. *J. Gen. Chem. USSR* 42, 1839-1854 (1972). Anal. calcd. for C$_{20}$H$_{36}$O: C, 82.13; H, 12.04. Found: C, 82.15; H, 12.51.

Ozonolysis and reduction of 4,5-Dihydroabienol 1b: as described in example 1 using 4,5-dihydroabienol 1b (5 g, 14 mmol) and sodium borohydride (1.94 g, 51 mmol). Standard work-up and flash chromatography as described gave 2.92 g (82%) of (−)-Sclareodiol 2a, 0.12 g (3%) of (+)-Sclareolide 4 and 0.12 g (3%) of Sclareacetal 5 as white solids.

EXAMPLE 5

Ozonolysis and Reduction of Abienol Acetate 1c

Z-(1R,2R,4aS,8aS)-1-(2-hydroxyethyl)-2,5,5,8a-tetra methyldecahydro-naphthalen-2-yl acetate) 1c

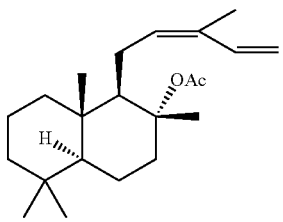

1c

Under nitrogen atmosphere N,N-dimethylaniline (10.4 g, 86 mmol) is added dropwise to Z-(+)-Abienol 55% (1a, 10 g, 19 mmol) at 50° C. followed by dropwise addition of acetyl chloride (6.8 g, 86 mmol) at 25-35° C. After 2 h at 50° C. the reaction mixture is poured upon 20% aqueous $H_2SO_4$. Extraction with t-butyl methyl ether, washing of the organic phase with conc. aqueous NaCl, drying over $MgSO_4$, filtration and evaporation of the solvent gives 9.6 g of a crude which is purified by flash chromatography over 400 g of silicagel using hexane/t-butyl methyl ether 9:1 as eluent, giving 3.75 g of Abienol acetate 1c (41%) with a purity of 69% according to standardized NMR.

Analytical data of 1c: $^1$H-NMR (CDCl$_3$, 400 MHz): 6.8-6.9 (m, 1H), 5.4 (m, 1H), 5.0-5.2 (2H), 2.55 (m, 1H), 2.3-2.4 (1H), 2.1-2.2 (1H), 1.87 (s, 3H), 1.8 (s, 3H), 1.8-1.9 (2H), 1.5-1.7 (4H), 1.47 (s, 3H), 0.9-1.45 (5H), 0.85 (s, 6H), 0.8 (s, 3H) ppm. $^{13}$C-NMR (CDCl$_3$, 400 MHz): 170.2 (s, OAc), 134.0 (d, alkene), 133.9 (d, alkene), 129.8 (s, alkene), 112.9 (t, alkene), 87.4 (s), 58.5 (d), 55.5 (d), 41.8 (t), 39.9 (t), 39.3 (s), 38.6 (t), 33.4 (q), 33.1 (s), 23.5 (t), 22.9 (q), 23.2 21.5 (q), 20.9 (q), 20.0 (t), 19.9 (q), 18.4 (t), 15.7 (q) ppm. MS (EI): 272 (10%, [M-HOAc]$^+$), 257 (5%, [M-HOAc-15]$^+$), 191 (17%), 178 (18%), 163 (9%), 148 (17%), 135 (21%), 134 (100%), 133 (14%), 121 (15%), 119 (73%), 109 (18%), 107 (17%), 105 (20%), 95 (24%), 93 (19%), 91 (16%), 81 (30%), 79 (17%), 69 (19%), 67 (11%), 55 (20%), 43 (43%), 41 (24%). IR (film): 2925 (m), 2870 (w), 1726 (s), 1643 (w), 1459 (w), 1441 (w), 1387 (m), 1367 (m), 1245 (s), 1188 (w), 1154 (w), 1126 (m), 1081 (w), 1066 (w), 1020 (m), 987 (w), 971 (w), 931 (w), 898 (m), 865 (w). The IR data are congruent to the ones described for this compound by P. F. Vlad et al. in *J. Gen. Chem. USSR* 39, 451 (1969).

Ozonolysis and reduction of abienol acetate 1c: as described in example 1 using abienol acetate 1c (2.5 g, 5.2 mmol) in ethanol (50 ml) and sodium borohydride (0.85 g, 22 mmol) in ethanol (10 ml). Standard work-up and flash chromatography over silicagel (70 g) using a hexane/ethyl acetate 5:1 to 2:1 gradient gave 1.5 g (10%) of sclaral acetate 6 and 1.13 g (73%) of sclareodiol acetate 2c ((1R,2R,4aS, 8aS)-1-(2-hydroxyethyl)-2,5,5,8a-tetramethyldeca-hy-dronaphthalen-2-yl acetate) as white solids.

The analytical data of sclaral acetate 6 (NMR, IR, MS) and sclareodiol acetate 2c (NMR, IR) are identical to the ones described in the literature, e.g. in *Synth. Comm.* 34, 3631 (2004) and *Australian J. Chem.* 25, 1767-1778 (1972). MS (EI) of 2c: 236 (34%, [M-HOAc]$^+$), 221 (50%, [M-HOAc-15]$^+$), 195 (9%), 192 (19%), 191 (35%), 177 (39%), 166 (9%), 165 (15%), 163 (13%), 151 (63%), 149 (17%), 138 (10%), 137 (44%), 136 (52%), 125 (20%), 124 (38%), 123 (63%), 121 (34%), 112 (56%), 110 (12%), 109 (95%), 107 (34%), 105 (13%), 97 (23%), 95 (100%), 93 (32%), 91 (16%), 85 (36%), 83 (29%), 82 (29%), 81 (69%), 79 (24%), 71 (26%), 69 (66%), 67 (33%), 60 ([HOAc$^+$], 4%), 57 (11%), 55 (38%), 43 (84%), 41 (43%).

EXAMPLE 6

Cyclization of Sclareodiol Acetate 2c to (−)-Ambrox 3

A mixture of dimethylcarbonate (0.12 g, 1.3 mmol) and NaOMe 30% in MeOH (0.25 g, 1.4 mmol) is added dropwise within 10 min to sclareodiol acetate 2c (0.25 g, 0.85 mmol) in water-free THF (5 ml) at reflux (65° C.). Another 10 ml THF are added to the white slurry. GC-analysis after 2 h at reflux shows complete conversion. After cooling to 25° C. the white suspension is poured onto water (25 ml) and is extracted with t-butyl methyl ether (2×25 ml). The organic layers are washed with water (25 ml), dried over MgSO$_4$, filtered and evaporated under reduced pressure. The residue (237 mg) is purified by flash chromatography over silicagel using hexane/ethyl acetate 5:1 as eluent to give after evaporation of the solvents 133 mg (67%) of (−)-Ambrox 3 and Sclareodiol 2a (4%) as white solids.

The analytical data of (−)-Ambrox 3 were identical to the ones known from the commercially available compound.

EXAMPLE 7

Ozonolysis and Reduction of Δ-Abienol 1d

Z-(1R,2R,4aS,8aS)-1-(3-cyclopropylbut-2-en-1-yl)-2,5,5,8a-tetramethyl-decahydro-naphthalen-2-ol) 1d

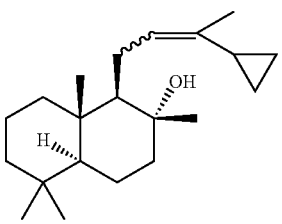

1d

Pd(acac)$_2$ (57 mg, 0.2 mmol, 0.5%) is added at 0° C. to a stirred mixture of Z-(+)-Abienol 55% (20 g, 37 mmol) in toluene (50 ml) and 40% aqueous KOH (30 ml). N-Nitroso-dimethylurethane 1.5 M in toluene (52 ml, 74 mmol) is added at 0-5° C. over 2 h. After 18 h at room temperature GC-analysis shows a 54% conversion to Δ-Abienol 1d. Phase separation and extraction with toluene (150 ml) gives an organic phase which is washed with 10% HOAc (100 ml), water (300 ml), 10% NaOH (100 ml) and brine (200 ml). Drying over MgSO$_4$, filtration and evaporation of the solvent under reduced pressure gives 21.6 g of a viscous brown oil which is dissolved in hexane/t-butyl methyl ether and filtered over a Buchner funnel loaded with 100 g of silicagel using a 100% hexane to hexane/t-butyl methyl ether 2:1 gradient as eluent, giving after evaporation of the solvents 13.7 g of a clear yellow oil which is subjected a second time to the same cyclopropanation procedure, giving after complete conversion (GC) and work-up 12.6 g of a clear yellow oil. Flash chromatography purification through 500 g SiO$_2$ using a hexane/t-butyl methyl ethyl 10:1→1:1 gradient gives 9.9 g Δ-Abienol 1d (58%) as colorless oil with a purity of 67% according to GC and istd NMR.

Analytical data of 1d: $^1$H-NMR (CDCl$_3$, 400 MHz): 5.4 (m, 1H), 2.45 (m, 1H), 2.15 (m, 1H), 1.1-1.9 (10H), 1.4 (s, 3H), 1.23 (s, 3H), 0.8-1.0 (4H), 0.88 (s, 3H), 0.85 (s, 3H), 0.82 (3H), 0.5-0.65 (5H, Δ) ppm. $^{13}$C-NMR (CDCl$_3$, 400 MHz): 133.9 (s, alkene), 128.2 (d, alkene), 71.8 (s), 61.8 (d), 56.1 (d), 43.6 (t), 41.9 (t), 37.6 (s), 33.5 (q), 33.3 (s), 24.6 (q), 23.1 (t), 21.6 (q), 20.1 (t), 18.8 (q), 18.7 (t), 15.4 (q), 12.3 (d), 2.3 (2 C, t) ppm. GCMS (EI): 286 (8%, [M-18]$^+$), 271 (4%), 191 (17%), 149 (15%), 148 (66%), 147 (12%), 135 (14%), 133 (45%), 123 (15%), 121 (25%), 119 (30%), 109 (29%), 108 (13%), 107 (33%), 105 (22%), 95 (100%), 94 (20%), 93 (44%), 92 (19%), 91 (27%), 83 (15%), 81 (30%), 79 (28%), 77 (16%), 71 (10%), 69 (41%), 67 (38%), 55 (34%), 43 (30%), 41 (34%). IR (film): 3454 (br), 3083 (w), 2922 (s), 2867 (m), 1648 (w), 1458 (m), 1442 (m), 1386 (m), 1364 (w), 1336 (w), 1317 (w), 1274 (w), 1188 (w), 1156 (w), 1125 (m), 1083 (m), 1066 (w), 1033 (m), 1015 (w), 997 (w), 972 (w), 936 (m), 924 (w), 909 (w), 883 (w), 847 (w), 817 (m), 722 (w).

Ozonolysis and reduction of Δ-Abienol 1d: as described in example 1 using Δ-Abienol 1d (2.5 g, 54 mmol) in ethanol (60 ml) and sodium borohydride (0.93 g, 24.6 mmol) in ethanol (10 ml). Standard work-up and flash chromatography through silicagel (70 g) using a hexane/ethyl acetate 2:1 to 100% ethyl acetate gradient gave 40 mg of (+)-Sclareolide 4 (3%) and 1.31 g (94%) of (−)-Sclareodiol 2a as white solids.

The invention claimed is:

1. A method of selective conversion of a compound of formula 1 to a compound of formula 2

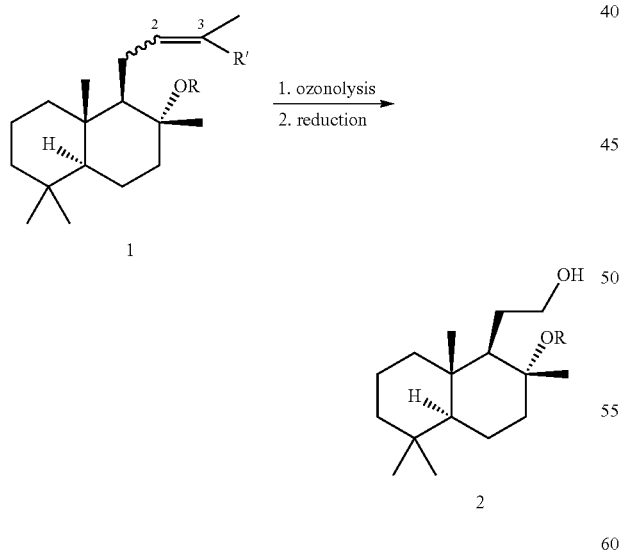

by an ozonolysis carried out at temperatures above −60° C. and a subsequent reduction,
wherein:
R is selected from H, acetals, aminals, alkyl groups, carboxylates, carbonates, carbamates, and any protecting group which can be attached to the compound of formula 1 or cleaved from the compound of formula 2, R' is selected from CH=CH$_2$, a C$_2$-C$_{20}$ alkyl moiety, a C$_3$-C$_{20}$ cycloalkyl moiety which may be alkylated, and a C$_3$-C$_{20}$ polycycloalkyl moiety which may be alkylated,
wherein in formula 1, the wavy bond depicts an unspecified configuration of the adjacent double bond between C2 and C3.

2. The method of claim 1 wherein the ozonolysis is carried out at a temperature above −20° C.

3. The method of claim 1 wherein the ozonolysis and/or the reduction takes place in a flow reactor.

4. The method of claim 1, wherein the ozonolysis and/or reduction takes place in a non-halogenated solvent or a mixture of non-halogenated solvents.

5. The method of claim 4 wherein the non-halogenated solvent is an alcoholic solvent comprising one or more –OH moieties.

6. The method of claim 4 wherein the non-halogenated solvent is ethanol.

7. The method of claim 1 wherein the ozonolysis takes place in a solvent, and the reduction takes place in the same solvent.

8. The method of claim 1, wherein a borohydride reducing agent is used in the reduction.

9. The method of claim 8 wherein NaBH4 is used as reducing agent in a concentration of 0.5-5 mol equiv.

10. The method of claim 1 which yields a compound of formula 2

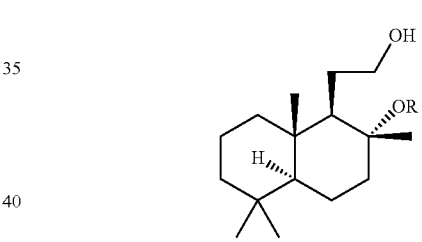

wherein:
R is selected from acetals, aminals, alkyl groups, carboxylates, acetates or formates, carbonates, carbamates, and any protecting group which can be cleaved from the compound of formula 2 to yield a compound of formula 2a

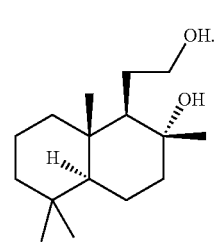

11. A method of preparing a compound of formula 3 by the steps of:
a) performing a selective conversion of a compound of formula 1 to a compound of formula 2 according to the steps of claim 1, b) subsequently performing a cyclization of the compound of formula 2 to yield a compound of formula 3

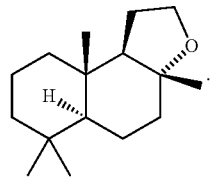

3

12. The method of claim 11, wherein the compound of formula 1 is protected on the OH-function and yields the corresponding compound of formula 2 protected on the OH-function.

13. The method of claim 12, wherein the compound of formula 2 protected on the OH-function is directly cyclized to the compound of formula 3.

14. The method of claim 12, wherein the compound of formula 2 protected on the OH-function, is deprotected and subsequently cyclized to the compound of formula 3.

15. A compound of formula 1d

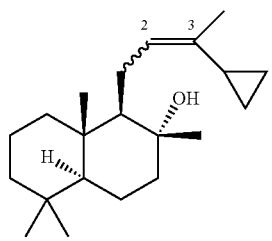

1d wherein the wavy bond depicts an unspecified configuration of the adjacent double bond between C2 and C3.

* * * * *